(12) United States Patent
Yeh et al.

(10) Patent No.: US 10,860,851 B2
(45) Date of Patent: Dec. 8, 2020

(54) HEAD MOUNTED DISPLAY APPARATUS AND EYE-TRACKING APPARATUS THEREOF

(71) Applicant: HTC Corporation, Taoyuan (TW)

(72) Inventors: Chia-Hua Yeh, Taoyuan (TW); Chun-Ta Lin, Taoyuan (TW); Fu-Cheng Fan, Taoyuan (TW)

(73) Assignee: HTC Corporation, Taoyuan (TW)

( * ) Notice: Subject to any disclaimer, the term of this patent is extended or adjusted under 35 U.S.C. 154(b) by 0 days.

(21) Appl. No.: 16/659,582

(22) Filed: Oct. 22, 2019

(65) Prior Publication Data
US 2020/0285849 A1 Sep. 10, 2020

Related U.S. Application Data

(60) Provisional application No. 62/813,760, filed on Mar. 5, 2019.

(51) Int. Cl.
| | | |
|---|---|---|
| *H04N 7/18* | (2006.01) | |
| *G06K 9/00* | (2006.01) | |
| *G02B 27/00* | (2006.01) | |
| *A61B 3/113* | (2006.01) | |
| *G02B 27/01* | (2006.01) | |

(52) U.S. Cl.
CPC ......... *G06K 9/00604* (2013.01); *A61B 3/113* (2013.01); *G02B 27/0093* (2013.01); *G02B 27/0172* (2013.01); *G06K 9/0061* (2013.01); *G02B 2027/0138* (2013.01)

(58) Field of Classification Search
CPC ............. G06K 9/00604; G06K 9/0061; G02B 27/0172; G02B 27/0093; G02B 2027/0138; A61B 3/113
USPC ............................................................ 348/78
See application file for complete search history.

(56) References Cited

U.S. PATENT DOCUMENTS

| | | | | |
|---|---|---|---|---|
| 4,867,542 A | * | 9/1989 | Shimazu | H04N 1/1911 359/310 |
| 6,188,510 B1 | * | 2/2001 | Edagawa | H04B 10/298 359/341.33 |
| 2013/0208362 A1 | * | 8/2013 | Bohn | G02B 27/017 359/630 |
| 2019/0041634 A1 | * | 2/2019 | Popovich | G01S 17/66 |
| 2019/0086674 A1 | * | 3/2019 | Sinay | G02B 27/0093 |
| 2019/0221191 A1 | * | 7/2019 | Chhipa | G09G 5/373 |

* cited by examiner

*Primary Examiner* — Shan E Elahi
(74) *Attorney, Agent, or Firm* — JCIPRNET

(57) ABSTRACT

A head mounted display apparatus and an eye-tracking apparatus thereof are provided. The eye-tracking apparatus includes a first wave guide apparatus, a voltage control beam splitter, a first beam splitter, and an image capture apparatus. The voltage control beam splitter provides a first light path between the image capture apparatus, the voltage control beam splitter, and a target zone according to a control signal during a first time period. The voltage control beam splitter provides a second light path between the image capture apparatus, the first wave guide apparatus, the first beam splitter, and the target zone according to the control signal during a second time period. The image capture apparatus respectively captures a first image and a second image of the target zone through the first light path and the second light path.

13 Claims, 4 Drawing Sheets

HEAD MOUNTED DISPLAY APPARATUS AND EYE-TRACKING APPARATUS THEREOF

CROSS-REFERENCE TO RELATED APPLICATION

This application claims the priority benefit of U.S. provisional application Ser. No. 62/813,760, filed on Mar. 5, 2019. The entirety of the above-mentioned patent application is hereby incorporated by reference herein and made a part of this specification.

BACKGROUND

Technical Field

The disclosure relates to a head mounted display apparatus and an eye-tracking apparatus, and more particularly to an eye-tracking apparatus having a single image capture apparatus.

Description of Related Art

Information confidentiality is very important in business, finance, and national security, especially nowadays when information is often shared in the cloud. In information confidentiality, iris recognition is undoubtedly the most credible confidentiality technology. Iris recognition is based on a camera and illuminating the eyeball with near-infrared light to capture a two-dimensional iris image of the eyeball to be processed into encrypted information. However, in today's technology field, the most common problem is how to prevent forgery. At present, methods of identifying real and fake eyeballs have improved hardware and software methods. The hardware method is to add more cameras to capture more eyeball information, causing hardware cost to increase. The software method is to add more algorithms, but the software method has manual processing doubts and is regarded as an indirect identification method having low credibility.

SUMMARY

The disclosure provides a head mounted display apparatus and an eye-tracking apparatus, which can effectively reconstruct a three-dimensional iris image.

The eye-tracking apparatus of the present invention includes a first wave guide device, a voltage control beam splitter, a first beam splitter, and an image capture apparatus. The voltage control beam splitter is disposed at a first end of the first wave guide device and a target zone is located outside a first side of the voltage control beam splitter. The first beam splitter is disposed at a second end of the first wave guide device. The image capture apparatus is located outside a second side of the voltage control beam splitter. The first side and the second side are different. The voltage control beam splitter provides a first light path between the image capture apparatus, the voltage control beam splitter, and the target zone according to a control signal during a first time period. The voltage control beam splitter provides a second light path between the image capture apparatus, the first wave guide device, the first beam splitter, and the target zone according to the control signal during a second time period. The image capture apparatus respectively captures a first image and a second image of the target zone through the first light path and the second light path.

The head mounted display apparatus of the present invention includes a body and the eye-tracking apparatus as described above. The eye-tracking apparatus is disposed in the body.

Based on the above, the eye-tracking apparatus of the present invention may produce a plurality of light paths through disposing the single image capture apparatus, the wave guide device, and the voltage control beam splitter, so as to capture images of the target zone through a plurality of different angles. Also, eyeball tracking of the target zone is executed by reconstructing a three-dimensional image using the plurality of images obtained.

To make the aforementioned and other features of the disclosure more comprehensible, several embodiments accompanied with drawings are described in detail as follows.

DETAILED DESCRIPTION OF DISCLOSED EMBODIMENTS

Figure 1:
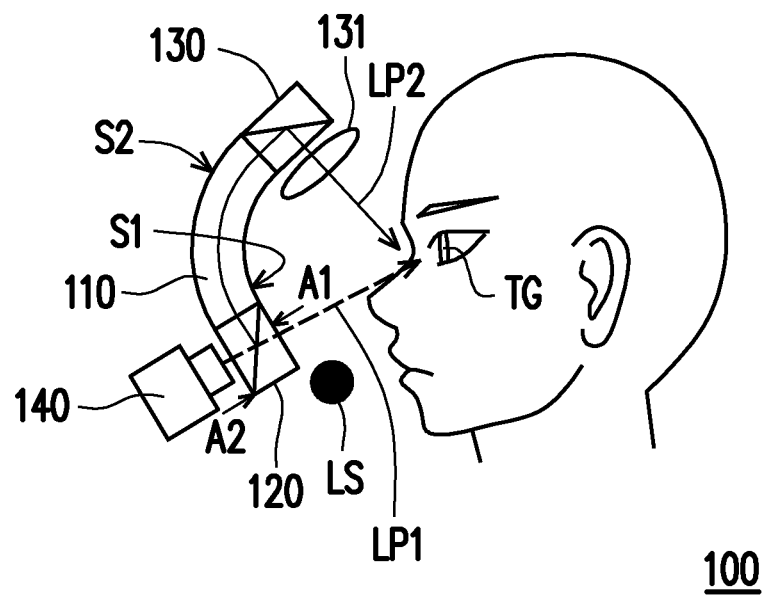
FIG. 1 is a schematic diagram of an eye-tracking apparatus according to an embodiment of the present invention.

Please refer to FIG. 1. FIG. 1 is a schematic diagram of an eye-tracking apparatus according to an embodiment of the present invention. An eye-tracking apparatus 100 includes a wave guide device 110, a voltage control beam splitter 120, a beam splitter 130, a lens 131, an image capture apparatus 140, and a light source LS. In the present embodiment, the wave guide device 110 has an arcuate structure. The voltage control beam splitter 120 is disposed on a first end S1 of the wave guide device 110 and the beam splitter 130 is disposed on a second end S2 of the wave guide device 110, wherein the first end S1 and the second end S2 are two different ends. In addition, a target zone TG is located outside a first side A1 of the voltage control beam splitter 120 and the image capture apparatus 140 is located outside a second side A2 of the voltage control beam splitter 120, wherein the first side A1 and the second side A2 are different. In the present embodiment, the target zone TG is the location of the user's eyes. The lens 131 is disposed between the beam splitter 130 and the target zone TG, and the lens 131 and the beam splitter 130 constitute an imaging apparatus.

Please note that the voltage control beam splitter 120 is a modulated beam splitter (MBS). The voltage control beam splitter 120 may receive a control signal which is an electrical signal and is configured as a light transmissive device or a reflective device according to the voltage value of the control signal. In the present embodiment, the voltage control beam splitter 120 may be configured as a light transmissive device according to the control signal during a first time period. At the same time, a first light path LP1 may be formed between the image capture apparatus 140, the voltage control beam splitter 120, and the target zone TG. The image capture apparatus 140 may capture a first image of an object (for example, the user's eyeball) on the target zone using the first light path.

On the other hand, the voltage control beam splitter 120 may be configured as a reflective device according to the control signal during a second time period. At the same time, a second light path LP2 may be provided between the image capture apparatus 140, the voltage control beam splitter 120, the wave guide device 110, the beam splitter 130, and the target zone TG. The image capture apparatus 140 may capture a second image of the object (the user's eyeball) on the target zone using the second light path LP2.

In the present embodiment, the first image and the second image are images of the user's eyeball respectively captured through different angles. Therefore, the first image and the second image may be provided as information for reconstructing a three-dimensional image, so as to obtain a three-dimensional image of the eyeball. Through the three-dimensional image of the eyeball, a model including eyeball depth, position, eyelid size, and three-dimensional iris characteristics can be constructed and a safety certification can be executed.

In addition, in the present embodiment, the light source LS is used to emit a light beam to the target zone TG and allow a reflective light spot to be generated on the user's eyeball. In this way, in the first image and the second image captured by the image capture apparatus 140, there may be images having the reflected light spot. Through the images of the reflected light spot in the first image and the second image, the movement state of the eyeball can be determined and tracking of the eyeball can be performed. In the present embodiment, the light source LS may be an infrared light source and the image capture apparatus 140 is a camera capable of capturing infrared images. Here, there is no specific limit on the location of the light source LS as long as the light source LS can effectively send the light beam to the target zone.

Please note that there is no order limitation on the first time period and the second time period described above. In the present embodiment, the first time period and the second time period may occur continuously or discontinuously. In addition, the voltage control beam splitter 120 may be implemented by applying a modulated beam splitter (MBS) known to persons skilled in the art without any particular limitation.

Figure 2:
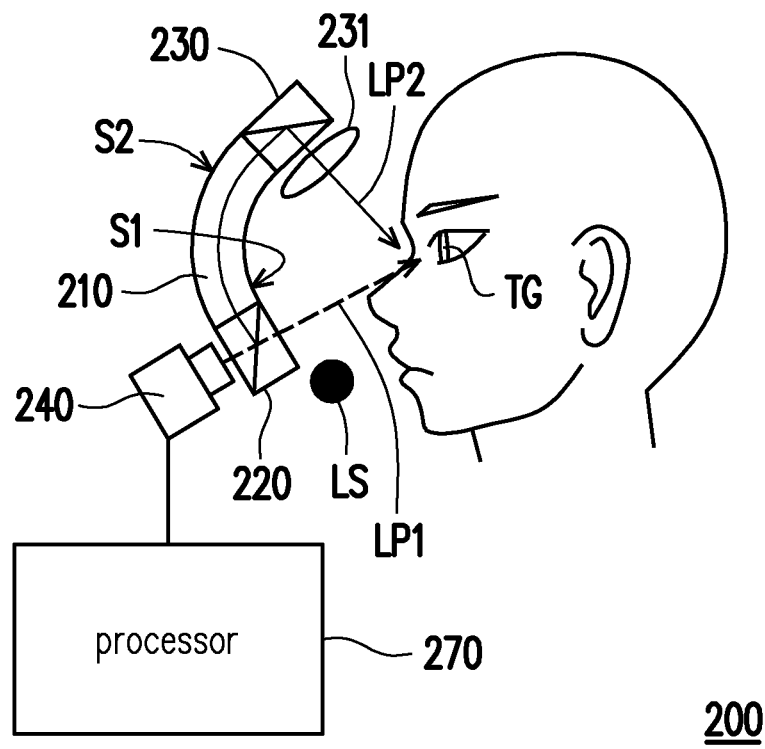
FIG. 2 is a schematic diagram of an eye-tracking apparatus according to another embodiment of the present invention.

Please refer to FIG. 2. FIG. 2 is a schematic diagram of an eye-tracking apparatus according to another embodiment of the present invention. An eye-tracking apparatus 200 includes a wave guide device 210, a voltage control beam splitter 220, a beam splitter 230, a lens 231, an image capture apparatus 240, a processor 270, and a light source LS. Unlike the embodiment of FIG. 1, in the present embodiment, the image capture apparatus 240 is coupled to the processor 270. The processor 270 receives a first image and a second image generated by the image capture apparatus 240, reconstructs a three-dimensional image according to the first image and the second image, and generates a three-dimensional image of a target zone TG.

In terms of hardware structure, the processor 270 may be a processor chip having computing power. Alternatively, the processor 270 may be a hardware circuit designed through a hardware description language (HDL) or any other digital circuit design method known to persons skilled in the art and implemented through a field programmable gate array (FPGA), a complex programmable logic device (CPLD), or an application-specific integrated circuit (ASIC).

Figure 3A:
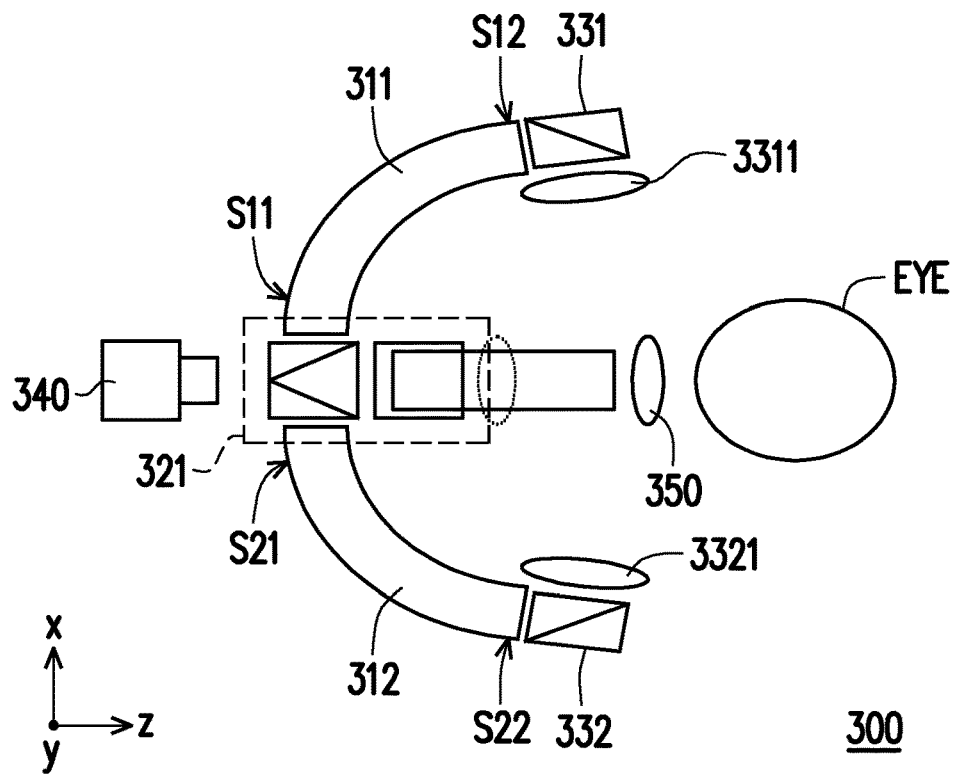
FIG. 3A is a schematic diagram of an eye-tracking apparatus according to another embodiment of the present invention.

Please refer to FIG. 3A for the following. FIG. 3A is a schematic diagram of an eye-tracking apparatus according to another embodiment of the present invention. An eye-tracking apparatus 300 includes wave guide devices 311 and 312, a voltage control beam splitter 321, beam splitters 331 and 332, an image capture apparatus 340, and lenses 3311, 3321, and 350. In the present embodiment, the wave guide devices 311 and 312 are disposed on the same plane, for example, the x-z plane of a three-dimensional coordinate system. First ends S11 and S21 of the wave guide devices 311 and 312 are adjacent to each other and the voltage control beam splitter 321 is disposed between the first ends S11 and S21 of the wave guide devices 311 and 312. The beam splitters 331 and 332 are respectively provided on second ends S12 and S22 of the wave guide devices 311 and 312. A target zone of the eye-tracking apparatus 300 has an object EYE (for example, an eyeball). The lens 3311 is disposed between the beam splitter 331 and the object EYE, the lens 3321 is disposed between the beam splitter 332 and the object EYE, and the lens 350 is disposed between the voltage control beam splitter 321 and the object EYE.

In terms of operation, the voltage control beam splitter 321 may be configured as a light transmissive device during a first time period and allow the image capture apparatus 340 to obtain a first image of the object EYE through a first light path between the voltage control beam splitter 321, the lens 350, and the object EYE. The voltage control beam splitter 321 may be configured as a reflective device during a second time period and allow a second light path to form between the image capture apparatus 340, the voltage control beam splitter 321, the wave guide device 311, the beam splitter 331, the lens 3311, and the object EYE. The image capture apparatus 340 may obtain a second image of the object EYE through the second light path. Moreover, the voltage control beam splitter 321 may be configured as a reflective device during a third time period and allow a third light path to form between the image capture apparatus 340, the voltage control beam splitter 321, the wave guide device 312, the beam splitter 332, the lens 3321, and the object EYE. The image capture apparatus 340 may obtain a third image of the object EYE through the third light path.

In the embodiment of the present invention, the first image, the second image, and the third image may be provided as information for reconstructing a three-dimensional image, so as to construct the three-dimensional image of the object EYE.

Figure 3B:
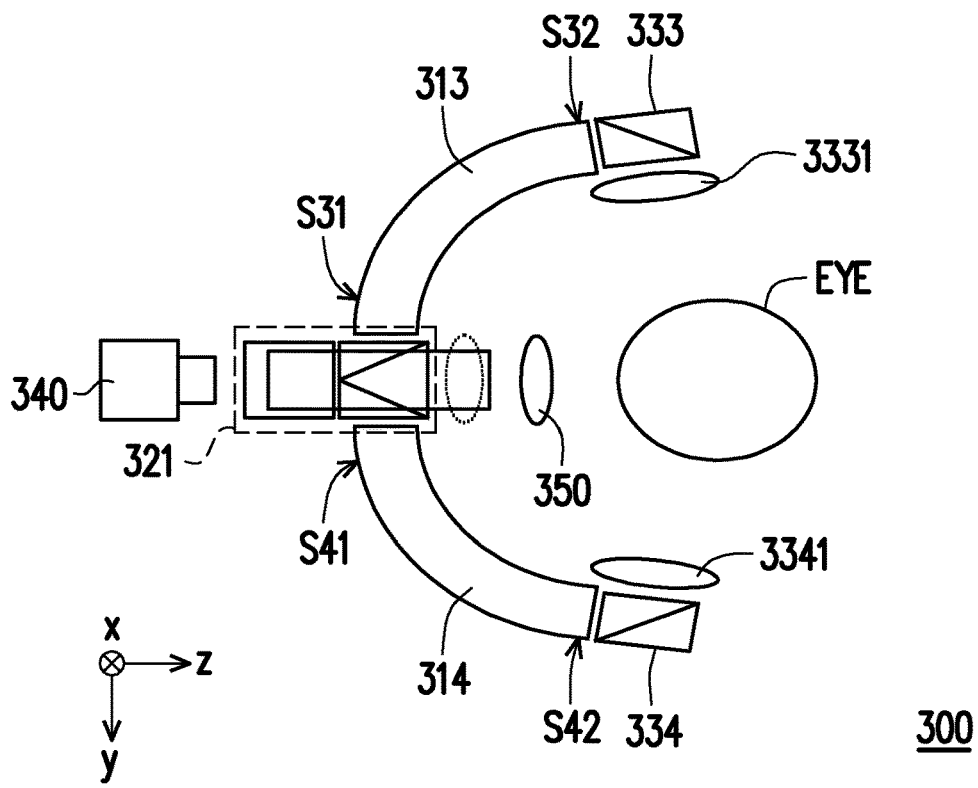
FIG. 3B is a schematic diagram showing an extended implementation method of the eye-tracking apparatus according to the embodiment of FIG. 3A of the present invention.

Next, please refer to FIG. 3B. FIG. 3B is a schematic diagram showing an extended implementation method of the eye-tracking apparatus according to the embodiment of FIG. 3A of the present invention. In FIG. 3B, the eye-tracking apparatus 300 further includes wave guide devices 313 and 314, beam splitters 333 and 334, and lenses 3331 and 3341. The wave guide devices 313 and 314 are disposed on another plane, for example, the y-z plane of a three-dimensional coordinate system. The plane in which the wave guide devices 311 and 312 of FIG. 3A are located (for example, a first plane) and the plane in which the wave guide devices 313 and 314 are located (for example, a second plane) do not overlap with each other, are not parallel to each other, and intersect at a straight line (for example, the z-axis).

First ends S31 and S41 of the wave guide devices 313 and 314 are adjacent to each other and the voltage control beam splitter 321 is disposed between the first ends S31 and S41 of the wave guide devices 313 and 314. The beam splitters 333 and 334 are respectively provided on second ends S32 and S42 of the wave guide devices 313 and 314. A target zone of the eye-tracking apparatus 300 has an object EYE (for example, an eyeball). The lens 3331 is disposed between the beam splitter 333 and the object EYE, and the lens 3341 is disposed between the beam splitter 334 and the object EYE.

In terms of operation details, following the operation details of FIG. 3A, the voltage control beam splitter 321 may be configured as a reflective device during a fourth time period and allow a fourth light path to form between the image capture apparatus 340, the voltage control beam splitter 321, the wave guide device 313, the beam splitter 333, the lens 3331, and the object EYE. The image capture apparatus 340 may obtain a fourth image of the object EYE through the fourth light path. Moreover, the voltage control beam splitter 321 may be configured as a reflective device during a fifth time period and allow a fifth light path to form between the image capture apparatus 340, the voltage control beam splitter 321, the wave guide device 314, the beam splitter 334, the lens 3341, and the object EYE. The image capture apparatus 340 may obtain a fifth image of the object EYE through the fifth light path.

In the embodiment of FIG. 3A and FIG. 3B, the voltage control beam splitter 321 is a multi-channel voltage control beam splitter and can adjust the traveling direction of the light beam according to control signals of different voltages.

The embodiment of FIGS. 3A and 3B of the present invention allows the single image capture apparatus 340 to capture images of different angles of the object EYE through the plurality of wave guide devices 311 to 314, so as to construct a more accurate three-dimensional image. In the image capturing of the embodiment of the present invention, the first light path to the fifth light path may be generated in a time-sharing manner to capture images of the plurality of different angles of the object EYE.

Figure 4A:
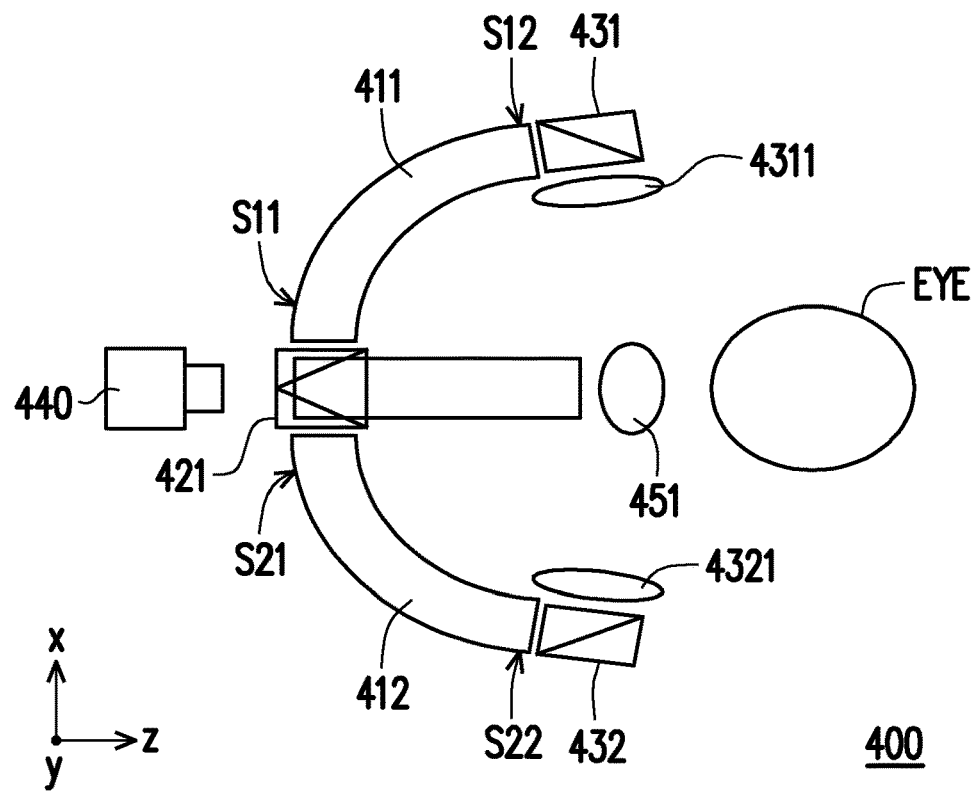
FIG. 4A and FIG. 4B are schematic diagrams of an eye-tracking apparatus according to another embodiment of the present invention.
Figure 4B:
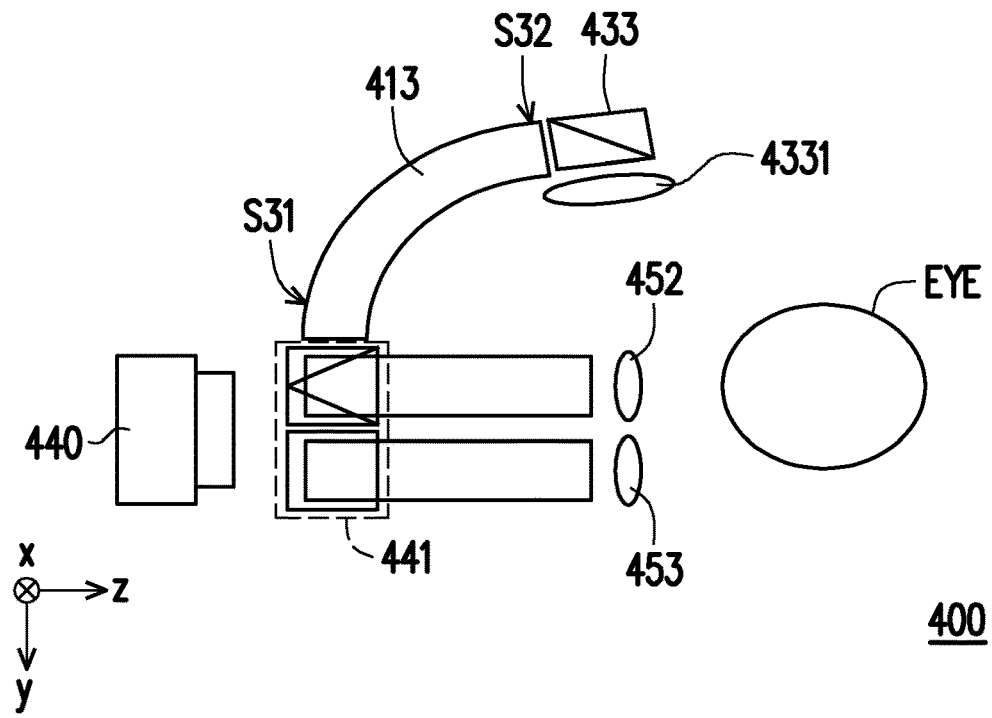

Please refer to FIG. 4A and FIG. 4B for the following. FIG. 4A and FIG. 4B are schematic diagrams of an eye-tracking apparatus according to another embodiment of the present invention. In FIG. 4A, an eye-tracking apparatus 400 includes wave guide devices 411 and 412, a voltage control beam splitter 421, beam splitters 431 and 432, an image capture apparatus 440, and lenses 4311, 4321, and 451. In the present embodiment, the wave guide devices 411 and 412 are disposed on the same plane, for example, the x-z plane of a three-dimensional coordinate system. First ends S11 and S21 of the wave guide devices 411 and 412 are adjacent to each other and the voltage control beam splitter 421 is disposed between the first ends S11 and S21 of the wave guide devices 411 and 412. The beam splitters 431 and 432 are respectively provided on second ends S12 and S22 of the wave guide devices 411 and 412. A target zone of the eye-tracking apparatus 400 has an object EYE (for example, an eyeball). The lens 4311 is disposed between the beam splitter 431 and the object EYE, the lens 4321 is disposed between the beam splitter 432 and the object EYE, and the lens 451 is disposed between the voltage control beam splitter 421 and the object EYE.

In terms of operation, through the light beam splitting of the voltage control beam splitter 421, the image capture apparatus 440 may capture a first image of the object EYE through the lens 451, a second image of the object EYE through the wave guide device 411, the beam splitter 431, and the lens 4311, and a third image of the object EYE through the wave guide device 412, the beam splitter 432, and the lens 4321.

In addition, in FIG. 4B, the eye-tracking apparatus 400 further includes a wave guide device 413, a beam splitter 433, a lens 4331, and a voltage control beam splitter 441. A first end S31 of the wave guide device 413 is adjacent to the voltage control beam splitter 441 for setting. The beam splitter 433 is disposed on a second end S32 of the wave guide device 413. The lens 4331 is disposed between the beam splitter 433 and the object EYE of the target zone. The lenses 441 and 453 are also disposed between the voltage control beam splitter 441 and the object EYE. In FIG. 4B, the wave guide device 413 is disposed on the y-z plane of a three-dimensional coordinate system.

Corresponding to the illustration of FIG. 4A, the voltage control beam splitter 441 of FIG. 4B and the voltage control beam splitter 421 of FIG. 4A may be the same member, but they have different perspectives. Also, the lens 453 and the lens 451 may be the same member. The voltage control beam splitters 421 and 441 are multi-channel voltage control beam splitters.

In the present embodiment, the voltage control beam splitter 441 may be configured as a light transmissive device or as a reflective device to transfer a light beam from one of the wave guide devices 411, 412, and 413 into the image capture apparatus 440. In FIG. 4B, during the fourth time period, the image capture apparatus 440 may capture the image of the object EYE and obtain a fourth image through the fourth light path formed between the voltage control beam splitter 441, the wave guide device 413, the beam splitter 433, the lens 4331, and the object EYE.

In the present embodiment, through the operation of the voltage control beam splitters 421 and 441, the image capture apparatus 440 may simultaneously obtain the first image to the fourth image through the first light path to the fourth light path. In the present embodiment, the first image to the fourth image may respectively be a partial image of four different regions of the object EYE. According to the first image to the fourth image, a more accurate three-dimensional image can be constructed.

Figure 5:
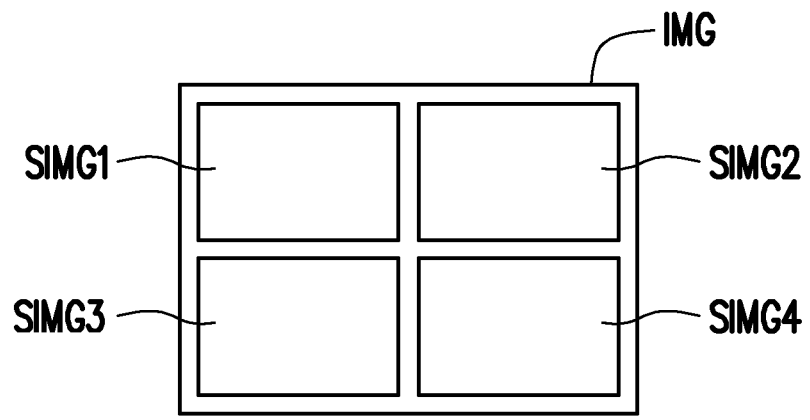
FIG. 5 is a schematic diagram of an image captured by an image capture apparatus according to an embodiment of the present invention.

Please refer to FIG. 5. FIG. 5 is a schematic diagram of an image captured by an image capture apparatus according to an embodiment of the present invention. In the embodiment of FIG. 4A and FIG. 4B, the first image to the fourth image captured by the image capture apparatus 440 may respectively be four complete images of the object EYE. Alternatively, in the embodiment of the present invention, the first image to the fourth image captured by the image capture apparatus 440 may be four partial images SIMG1 to SIMG4 in a complete image IMG of an object EYE as shown in FIG. 5. The eye-tracking apparatus can reconstruct a three-dimensional image of the object EYE according to the partial images SIMG1 to SIMG4.

In FIG. 5, the positional relationship of the partial images SIMG1 to SIMG4 in the complete image IMG is only an example. The positional relationship of the partial images SIMG1 to SIMG4 in the complete image IMG may be determined according to the positional relationship between the wave guide device and the object without any limitation.

Figure 6:
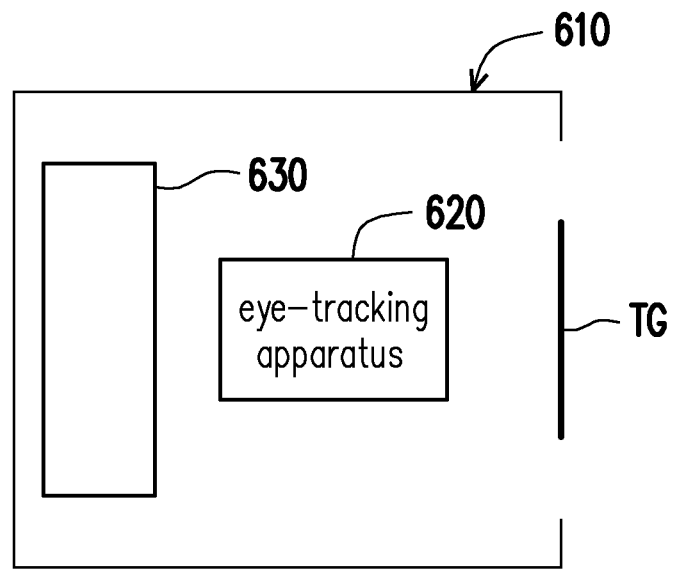
FIG. 6 is a schematic diagram of a head mounted display apparatus according to an embodiment of the present invention.

Please refer to FIG. 6 for the following. FIG. 6 is a schematic diagram of a head mounted display apparatus according to an embodiment of the present invention. A head mounted display apparatus 600 includes a body 610, an eye-tracking apparatus 620, and a display 630. Both the eye-tracking apparatus 620 and the display 630 are disposed in the body 610. The eye-tracking apparatus 620 is opposite to a target zone TG and is configured to detect the positional information of the user's eyeball on the target zone TG. The eye-tracking apparatus 620 may be implemented using the eye-tracking apparatus 100, 200, 300, or 400 as shown in FIGS. 1, 2, 3A, 3B, 4A, and 4B. Moreover, through images of a plurality of eyeballs generated by the eye-tracking apparatus 620, a three-dimensional image of the user's eyeball can be effectively constructed and iris information of the user's eyeball can be obtained, so as to be applied to safety certification.

In summary, the present invention allows a single image capture apparatus to capture images of a plurality of angles of a target zone object through one or more light guiding devices, thereby reconstructing a three-dimensional image, so as to effectively obtain a three-dimensional image information of an eyeball.

Although the disclosure has been disclosed in the above embodiments, the embodiments are not intended to limit the disclosure. It will be apparent to persons skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. An eye-tracking apparatus, comprising:
a first wave guide device;
a voltage control beam splitter, disposed at a first end of the first wave guide device, wherein a target zone is located outside a first side of the voltage control beam splitter;
a first beam splitter, disposed at a second end of the first wave guide device;
an image capture apparatus, located outside a second side of the voltage control beam splitter, the first side and the second side are different; wherein
the voltage control beam splitter provides a first light path between the image capture apparatus, the voltage control beam splitter, and the target zone according to a control signal during a first time period; the voltage control beam splitter provides a second light path between the image capture apparatus, the first wave guide device, the first beam splitter, and the target zone according to the control signal during a second time period; wherein the image capture apparatus respectively captures a first image and a second image of the target zone through the first light path and the second light path.

2. The eye-tracking apparatus according to claim 1, wherein the voltage control beam splitter is configured as a light transmissive device according to the control signal during the first time period and forms the first light path; the voltage control beam splitter is configured as a reflective device according to the control signal during the second time period and forms the second light path.

3. The eye-tracking apparatus according to claim 1, further comprising:
a processor, receiving the first image and the second image; the processor reconstructs a three-dimensional image according to the first image and the second image, and generates the three-dimensional image of the target zone.

4. The eye-tracking apparatus according to claim 1, further comprising:

a second wave guide device, disposed on a first plane same as the first wave guide device; the voltage control beam splitter being disposed at a first end of the second wave guide device; and
a second beam splitter, disposed at a second end of the second wave guide device; wherein
the voltage control beam splitter provides a third light path between the image capture apparatus, the second wave guide device, the second beam splitter, and the target zone according to the control signal during a third time period; and the image capture apparatus captures a third image of the target zone through the third light path.

5. The eye-tracking apparatus according to claim 4, further comprising:
a third wave guide device, wherein a first end of the third wave guide device is disposed adjacent to the voltage control beam splitter; and
a third beam splitter, disposed at a second end of the third wave guide device.

6. An eye-tracking apparatus according to claim 5, wherein the voltage control beam splitter provides a fourth light path between the image capture apparatus, the third wave guide device, the third beam splitter, and the target zone according to the control signal during a fourth time period and the image capture apparatus captures a fourth image of the target zone through the fourth light path.

7. The eye-tracking apparatus according to claim 6, wherein the first image to the fourth image are a plurality of partial images of different angles of the target zone.

8. The eye-tracking apparatus according to claim 6, wherein the first time period to the fourth time period may overlap with each other or may not overlap with each other.

9. The eye-tracking apparatus according to claim 6, further comprising:
a fourth wave guide device, wherein a first end of the fourth wave guide device is disposed adjacent to the voltage control beam splitter; and the fourth wave guide device is disposed on a second plane same as the third wave guide device; and
a fourth beam splitter, disposed at a second end of the fourth wave guide device; wherein
the voltage control beam splitter provides a fifth light path between the image capture apparatus, the fourth wave guide device, the fourth beam splitter, and the target zone according to the control signal during a fifth time period; and the image capture apparatus captures a fifth image of the target zone through the fifth light path.

10. The eye-tracking apparatus according to claim 9, wherein the first plane and the second plane intersect at a straight line.

11. The eye-tracking apparatus according to claim 9, wherein the voltage control beam splitter is a multi-channel voltage control beam splitter.

12. The eye-tracking apparatus according to claim 1, further comprising:
a first lens, disposed between the first beam splitter and the target zone; and
a second lens, disposed between the voltage control beam splitter and the target zone.

13. A head mounted display apparatus, comprising:
a body; and
an eye-tracking apparatus, disposed in the body, wherein the eye-tracking apparatus comprising:
a first wave guide device;

a voltage control beam splitter, disposed at a first end of the first wave guide device, wherein a target zone is located outside a first side of the voltage control beam splitter;

a first beam splitter, disposed at a second end of the first wave guide device;

an image capture apparatus, located outside a second side of the voltage control beam splitter, the first side and the second side are different; wherein the voltage control beam splitter provides a first light path between the image capture apparatus, the voltage control beam splitter, and the target zone according to a control signal during a first time period; the voltage control beam splitter provides a second light path between the image capture apparatus, the first wave guide device, the first beam splitter, and the target zone according to the control signal during a second time period; wherein the image capture apparatus respectively captures a first image and a second image of the target zone through the first light path and the second light path.

* * * * *